(12) United States Patent  (10) Patent No.: US 8,731,634 B2
Birman  (45) Date of Patent: May 20, 2014

(54) MEDICAL IMAGING SYSTEM AND PATIENT POSITIONING SYSTEM INCLUDING A MOVABLE TRANSPORT BELT

(75) Inventor: Yossi Birman, Haifa (IL)

(73) Assignee: General Electric Company, Schenectady, NY (US)

(*) Notice: Subject to any disclaimer, the term of this patent is extended or adjusted under 35 U.S.C. 154(b) by 1247 days.

(21) Appl. No.: 12/582,057

(22) Filed: Oct. 20, 2009

(65) Prior Publication Data

US 2011/0092792 A1   Apr. 21, 2011

(51) Int. Cl.
 *A61B 5/05* (2006.01)
(52) U.S. Cl.
 USPC ............. 600/407; 600/425; 5/128; 378/195
(58) Field of Classification Search
 USPC ................ 5/128; 600/425, 407; 378/195
 See application file for complete search history.

(56) References Cited

U.S. PATENT DOCUMENTS

| | | | |
|---|---|---|---|
| 4,131,802 A * | 12/1978 | Braden et al. | 378/20 |
| 6,895,105 B2 | 5/2005 | Wollenweber | |
| 7,020,315 B2 | 3/2006 | Vaisburd et al. | |
| 7,111,985 B2 | 9/2006 | Chao et al. | |
| 7,555,794 B2 | 7/2009 | Zelnik et al. | |
| 2006/0241408 A1 | 10/2006 | Yakubovsky et al. | |
| 2007/0050908 A1 | 3/2007 | Kogan et al. | |
| 2007/0055145 A1 | 3/2007 | Zelnik et al. | |
| 2007/0177713 A1 * | 8/2007 | Kohler et al. | 378/4 |
| 2009/0304249 A1 * | 12/2009 | Wu | 382/131 |

* cited by examiner

*Primary Examiner* — Unsu Jung
*Assistant Examiner* — Joel Lamprecht
(74) *Attorney, Agent, or Firm* — The Small Patent Law Group; Dean D. Small

(57) ABSTRACT

A medical imaging system for imaging a region of interest (ROI) in a patient. The imaging system includes an imaging modality unit having a field of view (FOV) and an examination platform. The examination platform has a pair of opposite ends and a platform surface extending therebetween along an examination axis. The platform surface extends into the FOV. The imaging system also includes a patient transport belt that is supported by the examination platform and extends along the platform surface between the ends of the examination platform. The imaging system also includes a motor that is operatively coupled to and configured to move the transport belt along the platform surface in a direction along the examination axis. The motor moves the transport belt so that a predetermined portion of the transport belt is within the FOV.

21 Claims, 8 Drawing Sheets

# MEDICAL IMAGING SYSTEM AND PATIENT POSITIONING SYSTEM INCLUDING A MOVABLE TRANSPORT BELT

BACKGROUND OF THE INVENTION

The subject matter disclosed herein relates generally to patient positioning and imaging systems and more particularly, to imaging systems capable of moving a patient between different axial positions to scan the patient.

Multi-modality imaging systems can scan a region of interest (ROI) of a patient using different imaging modalities. For example, multi-modality imaging systems may include Computed Tomography (CT), Magnetic Resonance Imaging (MRI), Positron Emission Tomography (PET), radiography, and/or Single Photon Emission Computed Tomography (SPECT) imaging systems. In these multi-modality imaging systems, the different modality units have respective field of views (FOVs) at different axial locations. During operation, a patient is moved to a first FOV where an image of the ROI is obtained and then moved to a second FOV where another image of the ROI is obtained. A doctor or medical technician (or the system) may then merge the data of the plurality of images from same or different modalities.

However, conventional multi-modality imaging systems may suffer from certain problems. For example, conventional multi-modality imaging systems use movable imaging pallets to transport the patient to one or more FOVs. The entire imaging pallet is supported in a cantilevered manner and moved (i.e., extended) into a bore of the imaging system. However, when the imaging pallet is extended into the bore, the imaging pallet may sag due to a weight of the patient. Such sagging may adversely affect the images of the ROI and may also adversely affect any processing of the data to merge the different images.

To address the sagging problem, conventional imaging pallet may have an increased thickness that is capable supporting the weight of heavy patients. However, the thickened imaging pallet may absorb more energy from the imaging system when an image of the ROI is obtained. This attenuation may distort or reduce the quality of the image. Furthermore, increasing a size of the imaging pallet may limit the ability of scanning detectors to move about the patient.

Also, depending upon the imaging modality being used, certain geometries of the imaging pallet may cause artifacts of the images. Accordingly, each imaging modality may require a different pallet geometry to reduce the artifacts. However, since the imaging pallet moves with the patient when the patient is moved between the different FOVs, it is difficult to change the geometry of the imaging pallet that supports the ROI of the patient.

BRIEF DESCRIPTION OF THE INVENTION

In one embodiment, a medical imaging system for imaging a region of interest (ROI) in a patient is provided. The imaging system includes an imaging modality unit having a field of view (FOV) and an examination platform. The examination platform has a pair of opposite ends and a platform surface extending therebetween along an examination axis. The platform surface extends into the FOV. The imaging system also includes a patient transport belt that is supported by the examination platform and extends along the platform surface between the ends of the examination platform. The imaging system also includes a motor that is operatively coupled to and configured to move the transport belt along the platform surface in a direction along the examination axis. The motor moves the transport belt so that a predetermined portion of the transport belt is within the FOV.

In another embodiment, a patient positioning system is provided that is configured to move a patient lying on an examination platform of an imaging system. The positioning system includes a patient transport belt that is configured to be supported by the examination platform and extend along a platform surface of the examination platform. The positioning system also includes a motor that is operatively coupled to and configured to move the transport belt along the platform surface in an axial direction. The motor moves the transport belt so that a predetermined portion of the transport belt is moved within a field-of-view (FOV) of the imaging system.

In a further embodiment, a method for imaging a region of interest (ROI) in a patient using an imaging system is provided. The imaging system includes a platform surface and a patient transport belt that is configured to move along the platform surface in an axial direction. The method includes sliding the transport belt along the platform surface to move a patient to a FOV associated with an imaging modality unit and scanning the ROI of the patient at the first FOV. Optionally, the method may include moving the patient to another FOV associated with a different imaging modality unit.

DETAILED DESCRIPTION OF THE INVENTION

The foregoing summary, as well as the following detailed description of certain embodiments of the present invention, will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" or "an embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
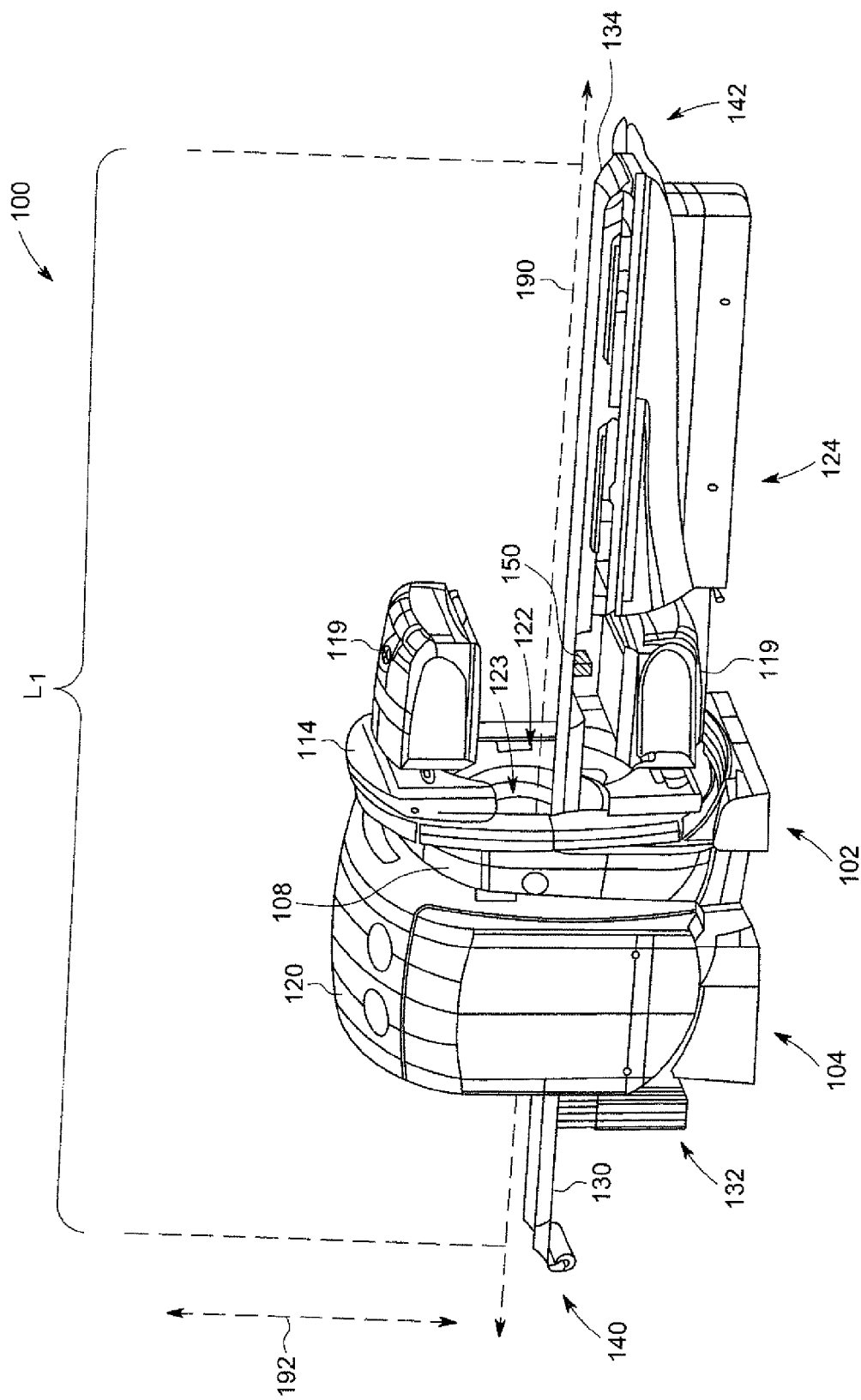
FIG. 1 is a side perspective view of an exemplary multi-modality imaging system formed in accordance with various embodiments.

Various embodiments of the invention provide an imaging system 100 as shown in FIG. 1. The imaging system 100 may be any type of imaging system, including a multi-modality imaging system. For example, the imaging system 100 may include different types of imaging modality units, such as a Positron Emission Tomography (PET) modality unit, a Single Photon Emission Computed Tomography (SPECT) modality unit, a Computed Tomography (CT) modality unit, an ultrasound modality unit, a Magnetic Resonance Imaging (MRI) modality unit, X-Ray radiography or fluoroscopy modality unit, and/or any other modality unit capable of generating images of a region of interest (ROI). In particular embodiments, the imaging system 100 is a medical imaging system. The various embodiments described herein are not limited to multi-modality medical imaging systems, but may also include single modality imaging systems, such as a stand-alone PET imaging system or a stand-alone SPECT imaging system. Moreover, the various embodiments are not limited to medical imaging systems for imaging human subjects, but may include veterinary systems. As used herein, the term "patient" may refer to a human patient or any other animal.

Referring to FIG. 1, the imaging system 100 is a multi-modality medical imaging system that includes a first modality unit 102 and a second modality unit 104. The first and second modality units 102 and 104 enable the imaging system 100 to scan a patient (not shown) in a first modality using the first modality unit 102 and to also scan the patient in a second modality using the second modality unit 104. The imaging system 100 allows for multiple scans in different modalities to facilitate an increased diagnostic capability over single modality systems. In one embodiment, the medical imaging system 100 is a Computed Tomography/Nuclear Medicine (CT/NM) imaging system. For example, the first modality unit 102 may be an NM imaging system and the second modality unit 104 may be a CT imaging system.

The imaging system 100 is also shown as including a gantry 108 that is associated with an NM imaging system and a gantry 120 that is associated with a CT imaging system. The gantry 108 includes a rotor 114 that supports NM cameras 119. The NM cameras 119 may be, for example, gamma cameras, SPECT detectors, and/or PET detectors. The rotor 114 is configured to rotate the NM cameras 119 about an examination axis 190 that may extend through a center of a bore 123 of the imaging system 100. The bore 123 may extend through the gantries 108 and 120 along the examination axis 190. The bore 123 is sized and shaped to allow a patient to be moved into and out of the bore 123.

The imaging system 100 also includes a patient positioning system 124 for moving the ROI of the patient to a predetermined or desired axial location along the examination axis 190. During operation of the imaging system 100, the positioning system 124 may move the patient in an axial direction (i.e., in a direction along the examination axis 190) through a central opening 122 of the bore 123.

Figure 2:
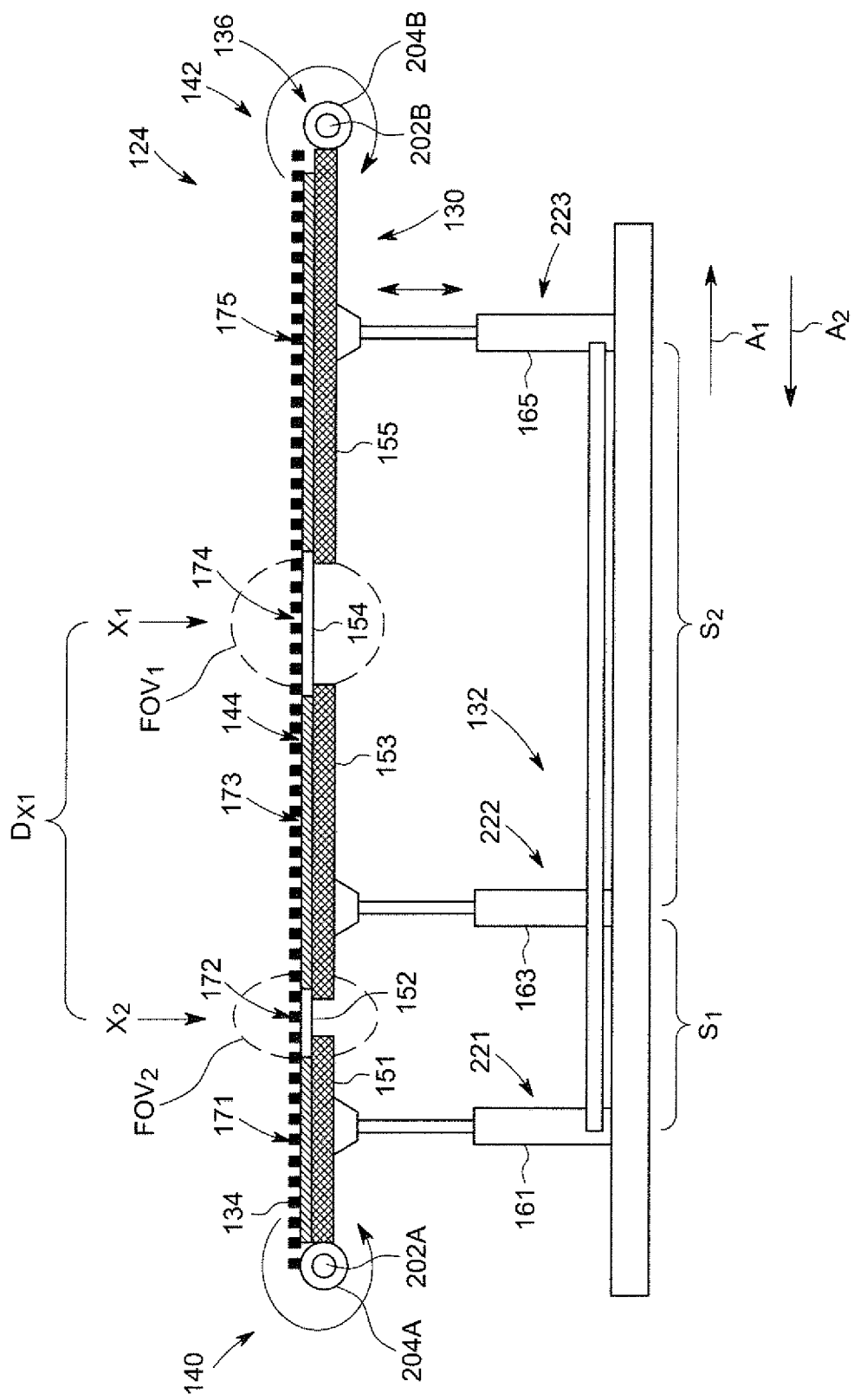
FIG. 2 is a side schematic view of a positioning system formed in accordance with various embodiments that may be used with the imaging system of FIG. 1.

As shown in FIG. 1, the positioning system 124 may include an examination pallet or platform 130, an actuator system 132, a patient transport belt 134, and a drive mechanism 136 (shown in FIG. 2). The examination platform 130 may support the transport belt 134 thereon that, in turn, may support a patient as the patient lies in a generally horizontal position (e.g., prone or supine position). As shown, the examination platform 130 has a pair of opposite ends 140 and 142 and a platform surface 144 (shown in FIG. 2) that extends between the ends 140 and 142 along the examination axis 190. The platform surface 144 may extend into a field-of-view (FOV) of at least one imaging modality unit.

The transport belt 134 is supported by the examination platform 130 and extends along the platform surface 144 between the ends 140 and 142. The transport belt 134 may be moved to move the patient along the examination axis 190 to a predetermined axial location. The actuator system 132 may move the examination platform 130 along a vertical axis 192 thereby moving the patient to a predetermined elevation. As such, the positioning system 124 may selectively move the patient along the examination axis 190 and along the vertical axis 192 to a desired spatial location for scanning the patient.

The platform surface 144 and the examination platform 130 may extend a track length $L_1$ (also referred to as a stroke distance) between the opposite ends 140 and 142. The patient may be moved throughout the track length $L_1$ during operation of the imaging system 100. In the exemplary embodiment, the track length $L_1$ does not change during operation of the imaging system 100. More specifically, the examination platform 130 does not include extendable portions that move along the examination axis 190 to change the track length $L_1$. However, in alternative embodiments, the examination platform 130 may include extendable portions that extend and retract to increase and decrease the track length $L_1$.

The imaging system 100 may also include a tracking device 150 that facilitates tracking a patient or determining a position of the patient relative to the modality units 102 and 104. The tracking device 150 may facilitate determining an axial location of the ROI relative to a respective modality unit. In some embodiments, the tracking device 150 may determine at least one of motion of the transport belt 134 and motion of the patient.

By way of example, the tracking device 150 may include a motion sensor, such as a light-emitting-diode (LED) sensor and/or a complimentary metal-oxide semiconductor (CMOS) sensor directed at a point of interest. More specifically, an LED may be directed to a point of interest on the transport belt 134 and bounce light off the transport belt 134 and onto a CMOS sensor. The CMOS sensor may send each image to a digital signal processor (DSP), which detects patterns in the images. The DSP examines how the patterns have moved since the previous image. Based on the change in patterns over a sequence of images, the DSP may determine how far the transport belt 134 has moved and send that information to a controller (not shown).

In such embodiments, when the transport belt 134 moves in the axial direction, the motion sensor communicates with the controller of the imaging system 100 to indicate movement of the transport belt and, thereby, indicate movement of the patient. Alternatively or in addition to, the tracking device 150 may include a transmitter (not shown) that is attached to the patient or a predetermined portion of the transport belt 134. Other tracking devices may be used that at least one of (a) track the patient or a predetermined portion of the transport belt 134 and (b) detect motion of the transport belt 134.

FIG. 2 is a side schematic view of the positioning system 124. The transport belt 134 is configured to move along the platform surface 144 so that a ROI of the patient may be scanned. For example, the transport belt 134 may move and hold the ROI at a predetermined axial location. the transport belt 134 may also move the ROI through a FOV at a predetermined rate as the ROI is being scanned. As another example, the transport belt 134 may be used with a point-and-shoot imaging system such that the transport belt 134 moves and holds the ROI at a predetermined axial location and then moves and holds the ROI at an adjacent predetermined axial location.

In some embodiments, the transport belt 134 is configured to move along the platform surface 144 so that a predetermined portion of the transport belt 134 may be positioned at a predetermined axial location. The predetermined portion, for example, may be a portion of the transport belt 134 that is associated with a location of the ROI of the patient (i.e., the ROI may be directly above the transport belt 134). As such, when the predetermined portion of the transport belt 134 is moved within a FOV of the imaging system, the ROI may also be moved within the FOV.

The transport belt 134 may translate along the platform surface 144 when moving the patient between different axial locations. For example, the transport belt 134 may slide on the platform surface 144 between different axial locations. In the exemplary embodiment, the platform surface 144 and the transport belt 134 may extend proximate to a $FOV_1$ of the modality unit 102 (FIG. 1) at a first axial location $X_1$. The platform surface 144 and the transport belt 134 may also extend proximate to a $FOV_2$ of the modality unit 104 (FIG. 1) at a second axial location $X_2$. The first and second axial locations $X_1$ and $X_2$ may be axially spaced apart from each other by an axial distance $D_{X1}$.

Furthermore, in some embodiments, the examination platform 130 may include a plurality of interconnected portions 151-155 that include platform portions 151, 153, and 155 and bridge portions 152 and 154. The interconnected portions 151-155 may be arranged end-to-end and axially aligned with each other. Each interconnected portion 151-155 includes a corresponding surface 171-175 that forms a portion of the platform surface 144. The surfaces 171-175 may be oriented and arranged with respect to each other so that the platform surface 144 is substantially level (i.e., the platform surface 144 may extend parallel to the examination axis 190 (FIG. 1)). The platform surface 144 may also be substantially smooth so that the transport belt 134 may slide on the platform surface 144 as the patient is moved to various axial locations.

However, in alternative embodiments, the examination platform 130 may be formed (e.g., molded) as one piece. For example, the examination platform may be formed from composite material, aluminum, or reinforced plastics.

The transport belt 134 may comprise a long flexible body that is capable of moving along the platform surface 144 when a force pulls or pushes the transport belt 134 in the axial direction. In particular embodiments, the transport belt 134 is capable of conforming to the platform surface 144 such that a cross-sectional shape of the transport belt 134 is substantially similar to a contour of the platform surface 144. The transport belt 134 may comprise a high strength material that is substantially wear resistance. For example, the transport belt 134 may include a fabric, such as Cordura® (nylon), Kevlar® (polyaramid polyparaphenylene terephthalamide), Mylar® (biaxially-oriented polyethylene terephthalate (boPET) polyester film) and the like. The transport belt 134 may comprise more than one layer or fabric. In other embodiments, the transport belt 134 may also be a composite comprising several elements. For example, the transport belt may comprise a chain having numerous interconnected links or segments. In such embodiments, the patient may rest upon the links or segments when moved between the axial locations.

Furthermore, the transport belt 134 may include a slider having opposite ends that are attached to, for example, a high strength material or chains for moving the slider. In such embodiments, the patient may rest upon the slider when moved between the axial locations. The transport belt 134 may also comprise any material and/or elements that may form a conveyor belt. Also, in some embodiments, the transport belt 134 may include a body that is transparent to imaging signals from one or more modality units.

The platform portions 151, 153, and 155 may be supported by vertical posts 161, 163 and 165, respectively. The bridge portion 152 may join the platform portions 151 and 153, and the bridge portion 154 may join the platform portions 153 and 155. In some embodiments, the bridge portions 152 and 154 are removably attached or removably mounted to the corresponding bridge portions. Such removable bridge portions may facilitate assembly or reconfiguration of the positioning system 124. As shown, the bridge portion 152 may be supported by ledges of the platform portions 151 and 153, and the bridge portion 154 may be supported by ledges of the platform portions 153 and 155. The platform portions 151, 153, and 155 may be sized, shaped, and formed from a material to provide rigid support of the patient.

In particular embodiments, the bridge portions 152 and 154 are located within the $FOV_1$ and $FOV_2$, respectively, of the imaging system 100. The bridge portions 152 and 154 may be sized, shaped, and formed from a material to reduce energy attenuation when the ROI of the patient is scanned. As will be described below, the bridge portions 152 and 154 may comprise a different material than the platform portions 151, 153, and 155. Furthermore, in some embodiments, the bridge portions 152 and 154 may have different cross-sectional shapes than the cross-sectional shapes of the platform portions 151, 153, and 155.

As shown in FIG. 2, the drive mechanism 136 may include at least one motor 202 and at least one roller 204 that are operatively coupled to the transport belt 134. In the exemplary embodiment, the drive mechanism 136 includes a pair of motors 202A and 202B that are positioned proximate to the ends 140 and 142, respectively. The motors 202A and 202B may be operatively coupled to rollers 204A and 204B. For example, the motors 202A and 202B may be drum motors in which the rollers 204A and 204B are drum shells of the drum motors. The rollers 204A and 204B may rotate about corresponding rotational axes.

The motors 202A and 202B may be directly coupled to the examination platform 130. In particular, the motor 202A may be directly connected to the examination platform 130 such that the motor 202A has a fixed relationship with respect to the examination platform 130. The roller 204A may also be directly connected to the examination platform 130. Likewise, the motor 202B may be directly connected to the examination platform 130 such that the motor 202B has a fixed relationship with respect to the examination platform 130. The roller 204B may also be directly connected to the examination platform 130. In such embodiments, the motors 202A and 202B may move with the examination platform 130. In particular embodiments, the motor 202A is directly coupled to the platform portion 151, and the motor 202B is directly coupled to the platform portion 155.

In some embodiments, at least a section of the transport belt 134 may move along the platform surface 144 in the axial direction and then be redirected. For example, the transport belt 144 may be redirected by flexing the transport belt 134 so that the transport belt 134 moves in a direction that is different than the axial direction. As shown in FIG. 2, the transport belt 134 may be redirected by curving the transport belt 134 about the rotational axes of the rollers 204A and 204B. More specifically, the transport belt 134 may be wound at least once about the rollers 204A and 204B. By way of example, when the transport belt 134 is moved in a first axial direction as indicated by the arrow $A_1$, the roller 204B may collect the transport belt 134 by winding the transport belt 134 about the roller 204B. The roller 204A may unwind the transport belt 134 from the roller 204A at such time. Similarly, when the transport belt 134 is moved in an opposite second axial direction as indicated by the arrow $A_2$, the roller 204A may collect the transport belt 134 by winding the transport belt 134 about the roller 204A. The roller 204B may unwind the transport belt 134 from the roller 204B at such time. Accordingly, the rollers 204A and 204B may redirect the transport belt 134 when the transport belt 134 is moved along the examination platform 130.

In some embodiments, the transport belt 134, the rollers 204, the motors 202, and the examination platform 130 may be disengaged from one another in order to access the medical imaging system 100 for servicing or replacing components of the imaging system 100.

Figure 3:
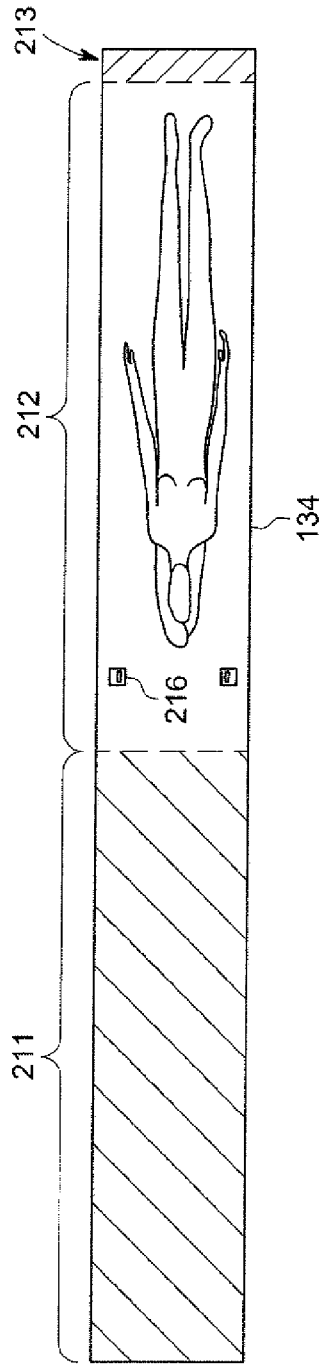
FIG. 3 is a plan view of a patient in a first axial position on a transport belt that may be used with the positioning system shown in FIG. 2.
Figure 4:
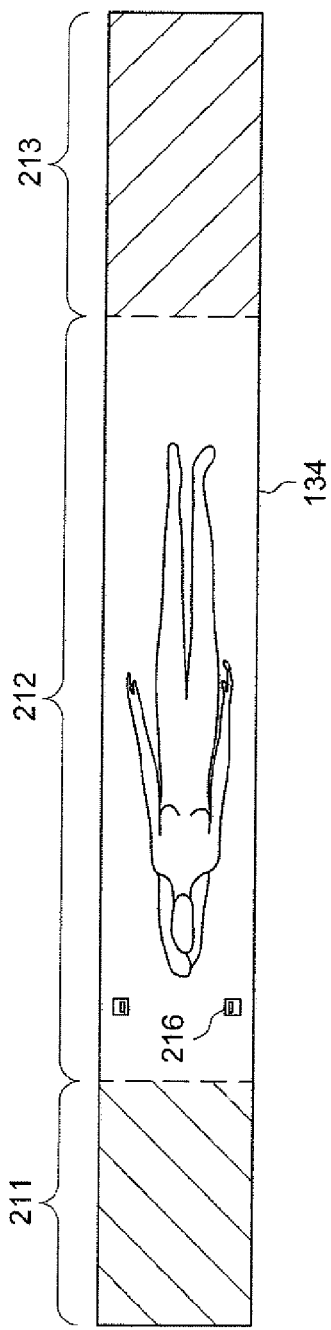
FIG. 4 is a plan view of the patient in a second axial position on the transport belt.
Figure 5:
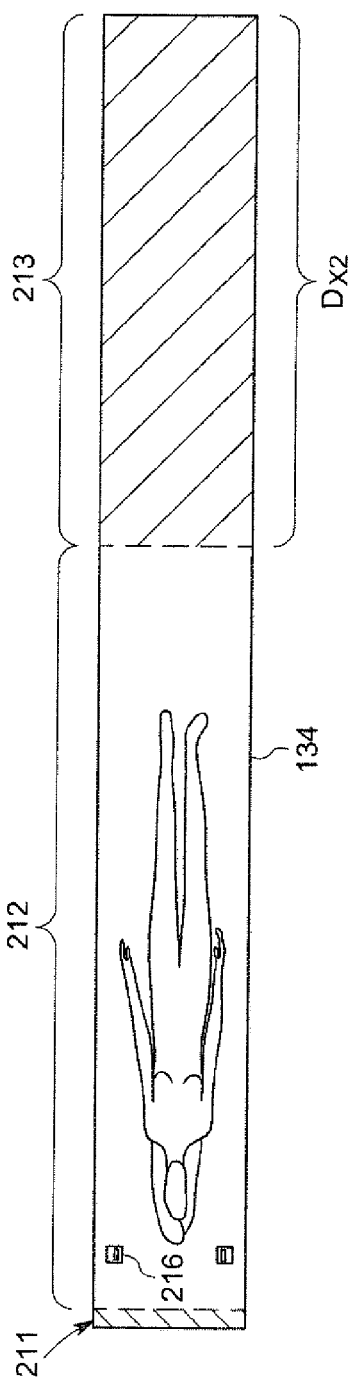
FIG. 5 is a plan view of the patient in a third axial position on the transport belt.

FIGS. 3-5 illustrate a patient in different axial positions during an imaging session. The transport belt 134 may include a plurality of belt sections 211-213. In some embodiments, the positioning system 124 (FIG. 2) may move the patient at most a maximum axial distance $D_{X2}$ (FIG. 5) along the track length $L_1$ (FIG. 1). As such, some of the belt sections may be redirected while other belt sections only move linearly along the platform surface 144 (FIG. 2). For example, in the illustrated embodiment, the transport belt 134 comprises a pair of end sections 211 and 213 and a body section 212 that extends between the end sections 211 and 213. The body section 212 may join the end sections 211 and 213.

The body section 212 may only move along the platform surface 144. In other words, the body section 212 may not be wound about either of the rollers 204 (FIG. 2). Furthermore, the end sections 211 and 213 may be configured to move on and off the platform surface 144 as shown in FIGS. 3-5 and be redirected (e.g., bent or flexed) by one of the rollers 204. For example, the end sections 211 and 213 may be configured to wind about the rollers 204A and 204B, respectively. Likewise, there may be rolled sections (not enumerated) that are directly attached to a corresponding roller that are never unwound from the corresponding roller.

In embodiments where the body section 212 only moves along the platform surface 144, the body section 212 may include a rigid or inflexible material configured to move along the platform surface 144 and the end sections 211 and 213 may comprise a flexible material. Furthermore, the body section 212 may include one or more fasteners 216 that facilitate coupling patient support accessories (not shown) to the transport belt 134. The support accessories may be removably attached to the transport belt 134. Examples of support accessories include a mattress, a head support, a head restraining device, a knee support, an arm support, a leg support, a pediatric cradle, straps, ECG connectors, and the like.

In alternative embodiments, the transport belt 134 may be similar to a conveyor belt that completely extends around the examination platform 130. More specifically, the transport belt 134 may comprise a loop that extends axially along the platform surface 144 from the end 140 to the end 142 and then curves to be under the examination platform 130 and then extend axially along the examination platform 130 to return to the end 140. Furthermore, in other embodiments, the transport belt 134 may be redirected along a side of the examination platform 130 or alongside or around the gantries by using directing rollers and the like.

In alternative embodiments, the positioning system 124 may comprise a plurality of smaller, individual positioning systems that each have a transport belt resting on a separate examination platform. The plurality of positioning systems may be arranged end-to-end with respect to each other. Each separate transport belt may be operatively coupled to a corresponding drive mechanism. As the patient is moved in the axial direction, the patient may move from a first transport belt on a first examination platform to a separate, second transport belt on a second examination platform. In such embodiments, the separate positioning systems may be moveable so that an operator may have access to different parts of the imaging system.

Returning to FIG. 2, the actuator system 132 may include a plurality of vertical actuators 221-223 that are configured to move the examination platform 130 to select elevations. More specifically, the vertical actuators 221-223 may move the examination platform 130 along the vertical axis 192 (FIG. 1) in a direction that is substantially perpendicular to the examination axis 190. The vertical actuators 221-223 may include the posts 161, 163, and 165, respectively. The posts 161, 163, and 165 may support the platform portions 151, 153, and 155, respectively. Although not shown, the vertical actuators 221-223 may include a motor or some other electric, hydraulic, or pneumatic mechanism to selectively move the posts 161, 163, and 165 to move the platform portions 151, 153, and 155.

Accordingly, the positioning system 124 may selectively move a patient along the examination axis 190 through the bore 123 (FIG. 1) to a desired axial location and also selectively position the patient at a desired elevation within the bore 123.

Furthermore, in some embodiments, the vertical actuators 221-223 may be operated individually so that the examination platform may rotate about a central axis. More specifically, the positioning system 124 may be operated to tilt the examination platform 130 so that the patient is oriented at an angle with respect to the examination axis 190.

Also shown in FIG. 2, the vertical actuators 221-223 (or the posts 161, 163, and 165) may be spaced apart from each other along the examination axis 190. More specifically, the vertical actuators 221 and 222 (or the posts 161 and 163) may have a spacing $S_1$ therebetween. The spacing $S_1$ may be sized and shaped to fit the modality unit 104 (FIG. 1) therebetween. The vertical actuators 222 and 223 (or the posts 163 and 165) may have a spacing $S_2$ therebetween. The spacing $S_2$ may be sized and shaped to fit the modality unit 102 (FIG. 1) therebetween.

Thus, the imaging system 100 may support a weight of the examination platform 130 and a weight of the patient at more than one axial location. In some embodiments, the imaging system 100 includes at least two vertical actuators (or posts) that are axially spaced apart from each other. As such, the imaging system 100 may reduce sagging or any unwanted vertical movement of the patient when the patient is moved along the examination platform 130.

Figure 6:
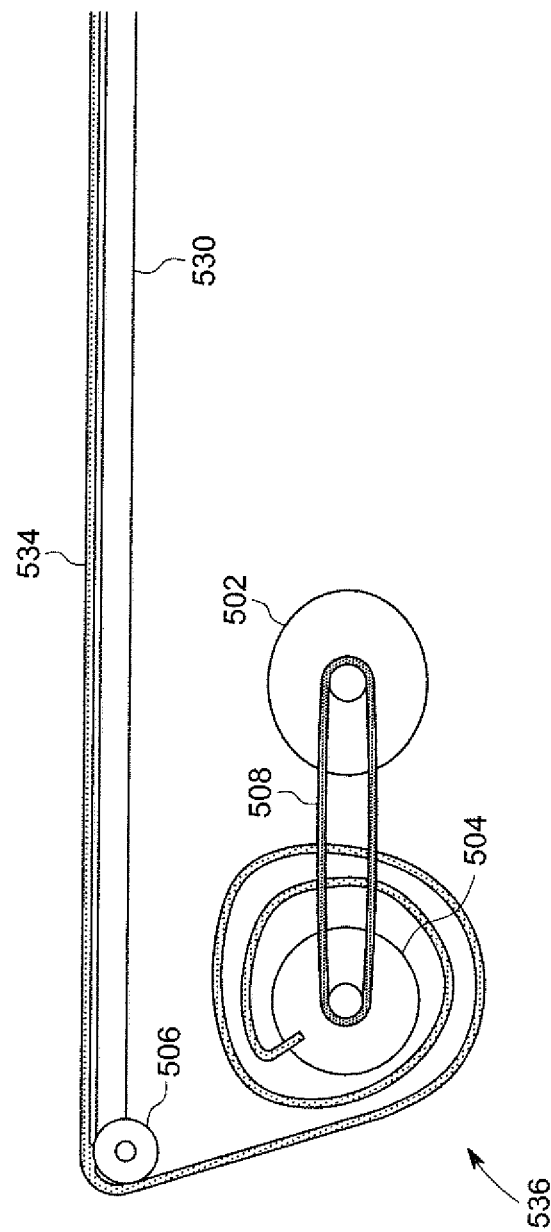
FIG. 6 illustrates an alternative drive mechanism that may be used with the positioning system shown in FIG. 1.

Furthermore, alternative drive mechanisms may be used with the positioning system 100. For example, FIG. 6 illustrates a drive mechanism 536 and shows a portion of an examination platform 530 and a transport belt 534. The transport belt 534 may be operatively coupled to a roller 504 under the examination platform 530. When in use, the transport belt 534 is redirected by an end roller 506 located at an end of the examination platform 530. The end roller 506 redirects the transport belt 534 to extend underneath the examination platform 530. The transport belt 534 may wind or spool about the roller 504 that is operatively coupled to a motor 502 through a drive belt 508. The end roller 506 and the roller 504 rotate when the motor 502 drives the drive belt 508.

Figure 7:
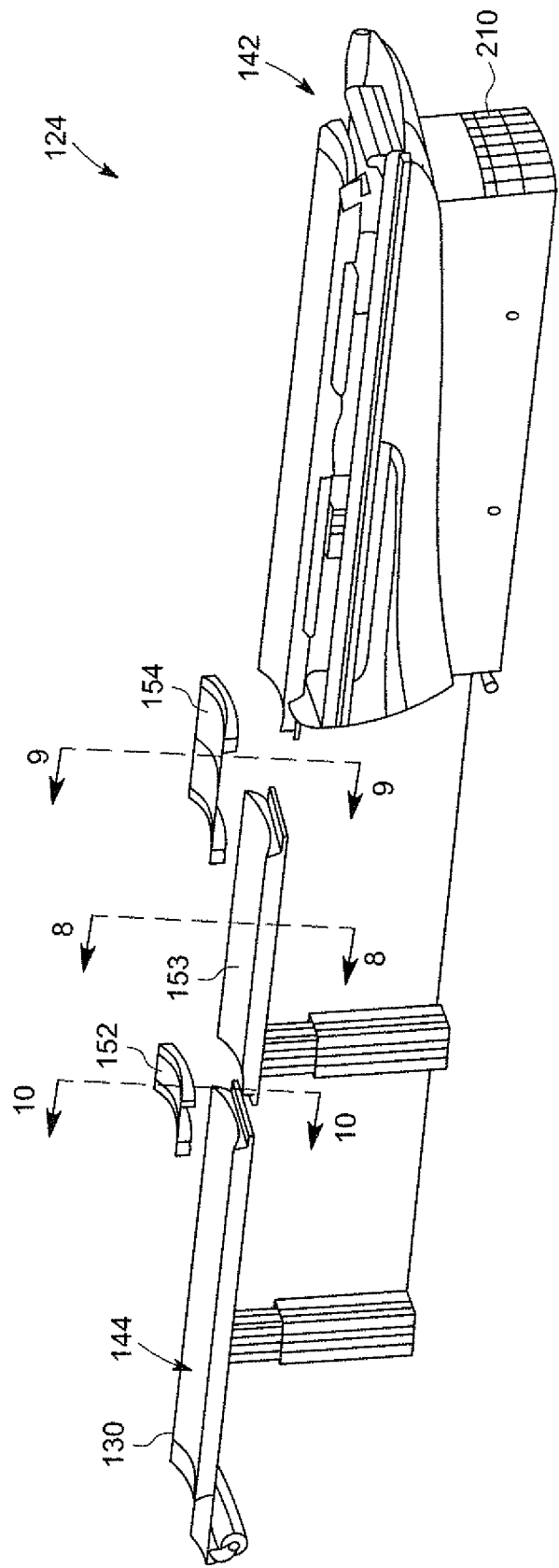
FIG. 7 is a partially exploded view of the positioning system shown in FIG. 2.

FIG. 7 is a partially exploded view of the positioning system 124. In the exemplary embodiment, the platform surface 144 of the examination platform 130 has a concave curvilinear contour (e.g., the platform surface 144 may be cradle-shaped). The transport belt 134 (FIG. 1) may be shaped or configured to conform to the shape of the platform surface 144. The curvilinear contour of the platform surface 144 may effectively hold or cradle the patient as the patient is moved in the axial direction. As such, the platform surface 144 may facilitate holding the patient in a desired orientation or prevent the patient from inadvertently rolling off the platform surface 144. In some embodiments, the surfaces 171-175 (FIG. 2) of the interconnected portions 151-155 (FIG. 2) are mirror-polished to reduce friction between the platform surface 144 and the transport belt 134 so that the transport belt 134 may slide smoothly over the platform surface 144.

Also shown, the positioning system 124 may include a system base 210 that houses at least one vertical actuator. The system base 210 may be sized to allow a patient to mount and demount the transport belt 134 on the examination platform 130. The system base 210 may extend at least to the end 142 of the examination platform 130. The transport belt 134 may be redirected into the system base 210.

In alternative embodiments, the system base 210 may include an individual positioning system as described above to facilitate the patient mounting or demounting the examination platform 130.

Figure 8:
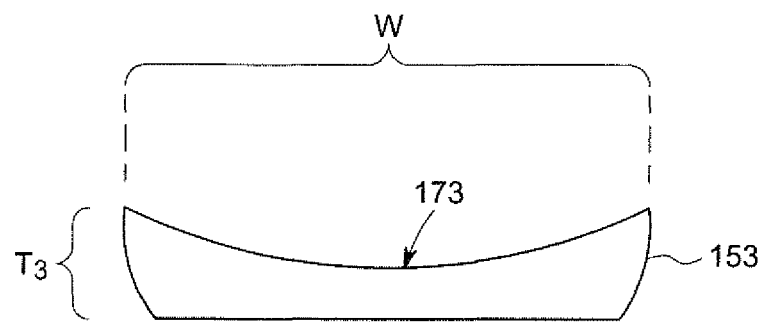
FIG. 8 illustrates a cross-section of an examination platform taken along the line 8-8 shown in FIG. 7.
Figure 9:
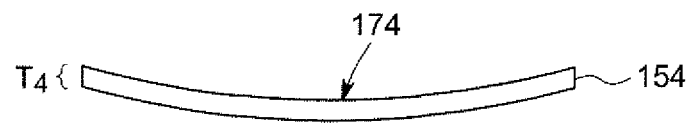
FIG. 9 illustrates another cross-section of the examination platform taken along the line 9-9 shown in FIG. 7.
Figure 10:
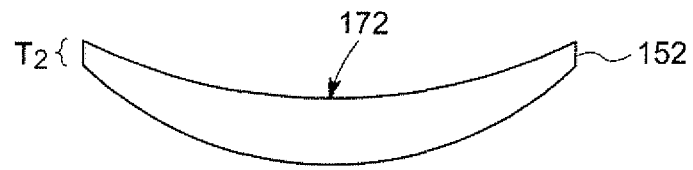
FIG. 10 illustrates another cross-section of the examination platform taken along the line 10-10 shown in FIG. 7.

FIGS. 8-10 illustrate different cross-sections of the examination platform 130 as shown in FIG. 7. FIG. 8 illustrates a cross-section of the platform portion 153 taken along the line 8-8. FIG. 9 illustrates a cross-section of the bridge portion 154 taken along the line 9-9, and FIG. 10 illustrates a cross-section of the bridge portion 152 taken along the line 10-10. The bridge portions 152 and 154 may have different cross-sectional shapes (e.g., thicknesses, geometries, contours) with respect to the platform portions 151, 153, and 155. The bridge portions 152 and 154 may also comprise a different material as the platform portions 151, 153, and 155.

Certain geometries of patient tables may cause formations or artifacts in images. One geometry may cause artifacts for a first modality unit, but not cause artifacts in a second modality unit. As such, the bridge portions 152 and 154 may also have different cross-sectional shapes with respect to each other. By way of example, the bridge portions 152 and 154 may be used with an NM modality unit and a CT modality unit, respectively.

More specifically, the surfaces 172 and 174 of the bridge portions 152 and 154 may have contours that are substantially similar to the contour of the surface 173 of the platform portion 153. Also shown, the platform portion 153 may have a thickness $T_3$ and the bridge portions 152 and 154 may have thicknesses $T_2$ and $T_4$, respectively. The thicknesses $T_2$ and $T_4$ may be different with respect to each other to accommodate different imaging modalities. The thickness $T_3$ may be configured to provide structural integrity to the examination platform 130 and to support the patient when lying thereon. In some embodiments, a thickness may be substantially uniform throughout a width W of the examination platform 130, such as the thickness $T_4$, or a thickness may vary throughout the width W, such as the thicknesses $T_2$ and $T_3$.

In alternative embodiments, the bridge portions 152 and 154 do not extend entirely along the width W of the examination platform. In other words, the bridge portions 152 and 154 may include an opening or hole. For example, alternative embodiments may have a pair of rails that are separated along the width W of the examination platform 130. The pair of rails may extend along the examination axis 190 and join adjacent platform portions. In such embodiments, the transport belt 134 (FIG. 1) may slide along the rails and be sturdy enough to support the patient. However, in the exemplary embodiment, the curvature of the platform surface 144 is substantially uniform throughout the examination platform 130.

Figure 11:
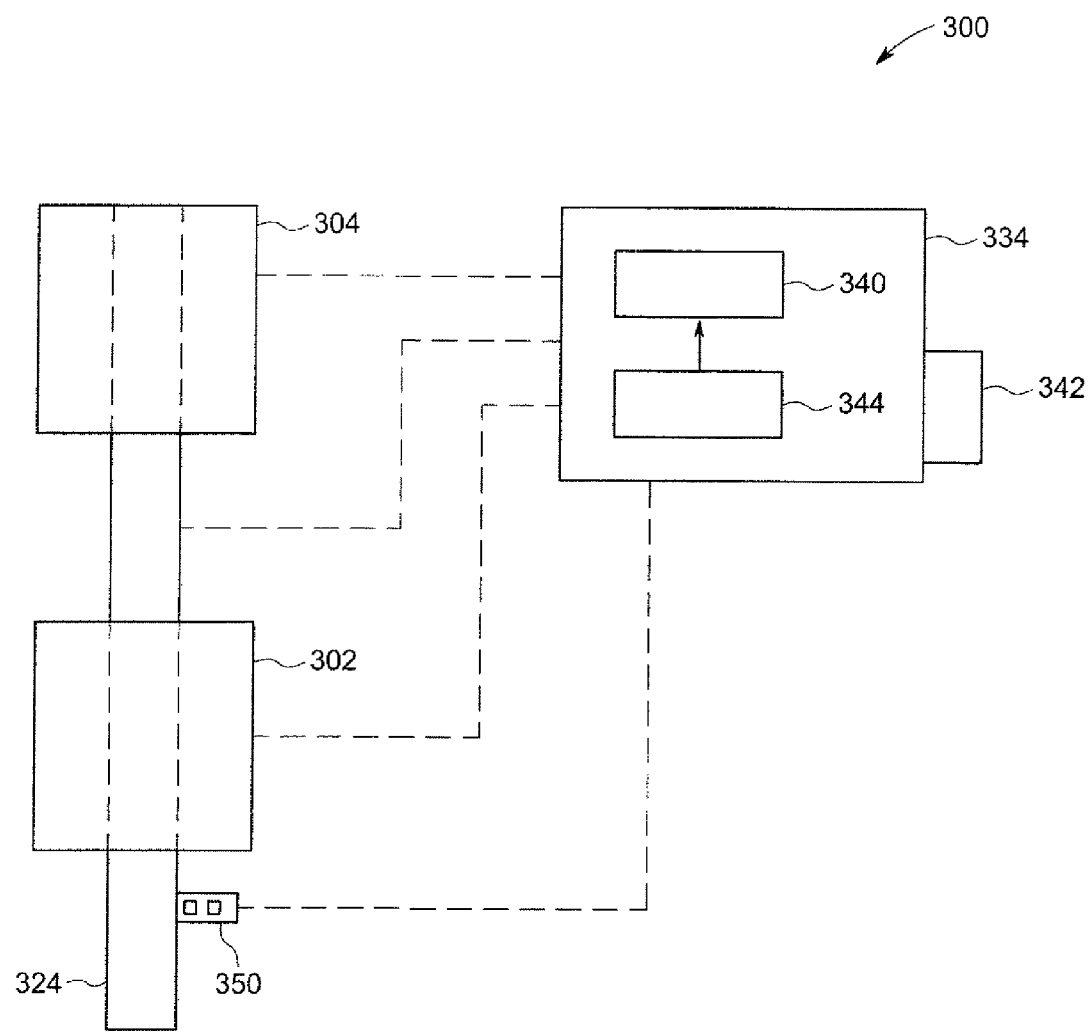
FIG. 11 is a block schematic diagram of an imaging system formed in accordance with various embodiments.

FIG. 11 is a block schematic diagram of an imaging system 300 that may be similar to the imaging system 100 illustrated in FIG. 1. The imaging system 300 may include a workstation 334 that is communicatively coupled to different modality units 302 and 304, a positioning system 324, and a tracking device 350 through one or more communication links (indicated as dashed lines). The communication links may be hardwired and/or wireless communication links. The workstation 334 may be, for example, a personal computer, laptop computer, or a handheld device. In the exemplary embodiment, the workstation 334 controls real-time operation of the components of the imaging system 300. The workstation 334 may also be programmed to perform medical image diagnostic acquisition and reconstruction processes.

The workstation 334 includes a central processing unit (CPU) or controller 340, a display 342 and an input device 344. As used herein, the term "controller" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. In the exemplary embodiment, the controller 340 executes a set of instructions that are stored in one or more storage elements or memories, in order to process input data. The storage elements may also store data or other information as desired or needed. The storage element may be in the form of an information source or a physical memory element within the controller 340.

The set of instructions may include various commands that instruct the controller 340 as a processing machine to perform specific operations such as methods and processes of various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The controller 340 receives user inputs, e.g., user commands, from the input device 344. The input device 344 may be, for example, a keyboard, mouse, a touch-screen panel, a voice recognition system, and the like. An operator may control the operation of the imaging system 300 through the input device 344. More specifically, an operator may control the positioning system 324 and the modality units 302 and 304 to perform one or more scans of a ROI of the patient. In addition, the operator may provide user inputs that initiate pre-programmed imaging sequences or protocols. Similarly, the operator may control the display of the resulting image on the display 342 and can perform image-enhancement functions using programs executed by the controller 340.

Figure 12:
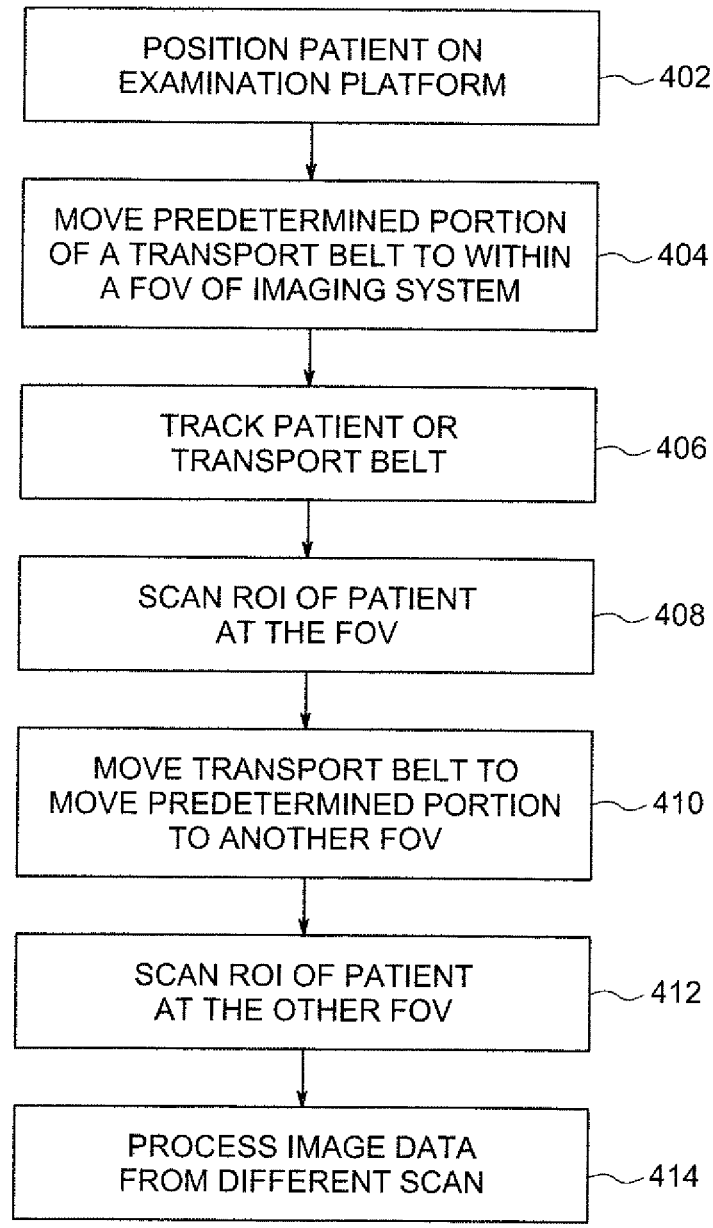
FIG. 12 is a block diagram of a method of imaging a region of interest (ROI) of a patient in accordance with various embodiments.

FIG. 12 is a block diagram of a method 400 of imaging a region of interest (ROI) in accordance with various embodiments. The method 400 may be used with a multi-modality imaging system, such as the imaging system 100 described above. The imaging system may include an examination platform that extends along an examination axis through a bore of the imaging system. The imaging system may also include first and second imaging modality units. The first imaging modality unit may have a FOV at a first axial location and the second imaging modality unit may have a FOV at a second axial location. The examination platform may extend proximate to both of the first and second FOV's.

At 402, a patient may be positioned on the examination platform. More specifically, the patient may be positioned on a movable patient transport belt that extends axially along a platform surface of the examination platform. The patient may be positioned in a known or desired location to facilitate tracking the patient. The patient may be in a home position or axial location. At 404, the transport belt may be moved in an axial direction along the platform surface so that a predetermined portion of the transport belt (or the patient) is within a FOV associated with one of the imaging modality units. More specifically, the predetermined portion of the transport belt may be moved to within the first FOV of the first modality unit.

At 406, at least one of the patient and the transport belt is tracked to determine a position of the patient with respect to the modality units. At 408, a ROI of the patient may be scanned at the first FOV. Image data of the ROI may be transmitted to a controller of the imaging system. At 410, the transport belt may be moved in the same axial direction along the platform surface so that the predetermined portion of the transport belt (or the patient) is within the second FOV. At 412, the ROI of the patient may be scanned with the second modality unit and the image data may be transmitted to the controller. At 414, the data from the first and second scans may be processed to provide separate images or may be processed to provide a composite image that includes data from both the first and second scans. At the end of the patient scanning session, the patient may be moved along the examination axis to the home position.

In alternative embodiments, the patient may be moved from a home position on one side of an imaging system through a bore of the imaging system to an exit position on an opposite side of the imaging system. For example, the patient may be moved in an axial direction from the home position to a first FOV within the bore. After the patient is scanned at the first FOV, the patient may be moved in the same axial direction to a second FOV. After the patient is scanned at the second FOV, the patient may be moved in the same axial direction to the exit position where the patient may demount the examination platform.

It is to be understood that the above description is intended to be illustrative, and not restrictive. For example, the above described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A medical imaging system for imaging a region of interest (ROI) of a patient, the imaging system comprising:
   an imaging modality unit having a field of view (FOV);
   an examination platform having a pair of opposite ends and a platform surface extending therebetween along an examination axis, the platform surface extending through the FOV; and
   a patient transport belt being supported by the examination platform and extending along the platform surface between the ends of the examination platform, the transport belt being movable along the platform surface into the FOV such that the transport belt is scanned by the imaging modality unit with the patient;
   wherein the examination platform comprises first and second platform portions and a bridge portion that extends between and joins the first and second platform portions, the bridge portion being located within the FOV of the imaging modality unit and having a fixed relationship with respect to the imaging modality unit when the transport belt moves the patient through the FOV, wherein the bridge portion has a different cross-sectional shape and comprises a different material with respect to the first and second platform portions.

2. The imaging system in accordance with claim 1 wherein the transport belt slides on the platform surface in the FOV when moved through the FOV.

3. The imaging system in accordance with claim 1 wherein the transport belt includes a flexible material that permits the transport belt to conform to a contour of the platform surface.

4. The imaging system in accordance with claim 3 wherein the platform surface has a curvilinear contour that is shaped to hold a patient.

5. The imaging system in accordance with claim 1 further comprising a motor operatively coupled to the transport belt, the motor moving the transport belt along the platform surface in a direction along the examination axis.

6. The imaging system in accordance with claim 1 further comprising a patient support accessory mounted onto the examination platform, the transport belt being coupled to and moving the patient support along the platform surface.

7. The imaging system in accordance with claim 1 further comprising a roller configured to redirect the transport belt, the transport belt curving about a rotational axis of the roller when the roller is rotated in one direction.

8. The imaging system in accordance with claim 1 wherein the transport belt comprises a pair of end sections and a body section that extends between the end sections, the body section only moving along the platform surface, the body section comprising a material that is more rigid than the end sections.

9. The imaging system in accordance with claim 1 further comprising a plurality of vertical actuators configured to move the examination platform to different elevations, the vertical actuators moving the examination platform in a direction that is substantially perpendicular to the examination axis.

10. The imaging system of claim 1, wherein the FOV is located at an imaging axial location and wherein the transport belt is redirected at front and back axial locations, the imaging axial location being located between the front and back axial locations, the transport belt being redirected by flexing or bending the transport belt so that the transport belt moves in a different direction.

11. The imaging system of claim 1, wherein the transport belt includes first and second belt sections and a body section that extends between the first and second belt sections, the first belt section being positioned before the FOV and the second belt section being positioned after the FOV, each of the first and second belt sections comprising a flexible material, wherein the body section includes a material that is more rigid than the belt sections and is positionable within the FOV.

12. The imaging system of claim 1, wherein the bridge portion is removably mounted to the first and second platform portions.

13. A method for imaging a region of interest (ROI) in a patient using an imaging system, the imaging system comprising an examination platform having a pair of opposite ends and a platform surface extending therebetween along an examination axis, the imaging system also comprising a patient transport belt configured to move along the platform surface in an axial direction, the method comprising:
sliding the transport belt along the platform surface so that a predetermined portion of the transport belt moves through a FOV of the imaging system; and
scanning the ROI of the patient at the FOV while the transport belt is in the FOV;
wherein the examination platform comprises first and second platform portions and a bridge portion that extends between and joins the first and second platform portions, the bridge portion being located within the FOV of the imaging system and having a fixed relationship with respect to the imaging system as the transport belt moves the patient through the FOV, wherein the bridge portion has a different cross-sectional shape and comprises a different material with respect to the first and second platform portions.

14. The method in accordance with claim 13 wherein the sliding the transport belt includes rotating rollers that are operatively coupled to the transport belt, the transport belt being redirected by the rollers.

15. The method in accordance with claim 13 wherein the FOV is a first FOV, the method further comprising:
sliding the transport belt along the platform surface so that the predetermined portion of the transport belt moves into a second FOV of the imaging system, the first and second FOVs being spaced apart and corresponding to different imaging modality units; and
scanning the ROI of the patient at the second FOV while the transport belt is within the second FOV.

16. A medical imaging system comprising:
an examination platform having a pair of opposite ends and extending along an examination axis between the pair of ends;
first and second imaging modality units, each of the first and second imaging modality units having a respective field-of-view (FOV), wherein the FOV of the first imaging modality unit has a first axial location along the examination axis and the FOV of the second imaging modality unit has a second axial location along the examination axis, the first and second axial locations being spaced apart; and
a patient transport belt being supported by the examination platform and extending therealong, the transport belt being movable along the examination axis through each of the FOVs of the first and second imaging modality units, the transport belt being scanned with the patient in the FOVs of the first and second imaging modality units;
wherein the examination platform comprises first and second platform portions and a bridge portion that extends between the first and second platform portions, the bridge portion being located within the FOV of the first imaging modality unit and having a fixed relationship with respect to the first imaging modality unit as the transport belt moves the patient through the FOV of the first imaging modality unit, wherein the bridge portion has a different cross-sectional shape and comprises a different material with respect to the first and second platform portions.

17. The imaging system of claim 16, wherein the transport belt is redirected at third and fourth axial locations, the first and second axial locations being located between the third and four axial locations, the transport belt being redirected by flexing or bending the transport belt so that the transport belt moves in a different direction.

18. The imaging system of claim 17, wherein the transport belt is at least one of directed underneath the examination platform or wound about a roller when the transport belt is flexed or bent.

19. The imaging system of claim 16, wherein the bridge portion is a first bridge portion and the examination platform includes a second bridge portion, the second bridge portion being located within the respective FOV of the second imaging modality unit.

20. The imaging system of claim 19, wherein the first imaging modality unit is a nuclear medicine (NM) imaging modality unit and the second imaging modality unit is a Computed Tomography (CT) imaging modality unit.

21. The imaging system of claim 19, wherein the first and second bridge portions have different cross-sectional shapes.